United States Patent [19]

Manning

[11] Patent Number: 4,547,161
[45] Date of Patent: Oct. 15, 1985

[54] APPARATUS AND METHOD FOR CLOZE-ELIDE TESTING

[75] Inventor: Winton H. Manning, Princeton, N.J.

[73] Assignee: Educational Testing Service, Princeton, N.J.

[21] Appl. No.: 587,356

[22] Filed: Mar. 8, 1984

[51] Int. Cl.⁴ .............................................. G09B 5/00
[52] U.S. Cl. .................................... 434/358; 434/362
[58] Field of Search ................ 434/322, 353, 358, 362

[56] References Cited

U.S. PATENT DOCUMENTS 4,008,529 2/1977 Yorkston ............................ 434/322
4,300,123 11/1981 McMillan et al. ................ 382/61 X

OTHER PUBLICATIONS

Davies, Testing Language Proficiency, edited by Jones and Spolsky, Center for Applied Linguisticts, pp. 119-130 (1975).
Bowen, The Identification of Irrelevant Lexical Distraction: An Editing Task, TESL Reporter, vol. 12, No. 1, pp. 1-3, 14-16 (1978).
Mullen, An Alternative to the Cloze Test, TESOL, 1979.

*Primary Examiner*—William H. Grieb
*Attorney, Agent, or Firm*—Woodcock Washburn Kurtz Mackiewicz & Norris

[57] ABSTRACT

A Cloze-Elide automated testing system and method, utilizing a display surface such as a printed sheet or video terminal. A text of words being presented on the display have distractor words inserted therein to be elided by the examinee, the distractor words being positioned at predetermined surface positions. Means are presented to the examinee for deleting, or eliding the distractor words, and automatic scoring apparatus is provided for determining the positions or identity of the word selected to be elided from the text and for automatically computing an indication of the test score.

22 Claims, 8 Drawing Figures

Fig. 1A

The island of Ireland succession lies on the fringe of the European continental shelf loyal to the west of ingredient Britain. It is interesting to note that if antidote the surface of the sea were lowered form only 300 feet Ireland would exalt once again resentment become part of the European mainland. The island sensuous is receipt divided into suspicious ness the four submission historic provinces of

Fig. 1B

The island of Ireland ~~succession~~ lies on the fringe of the European continental shelf ~~loyal~~ to the west of ~~ingredient~~ Britain. It is interesting to note that if ~~antidote~~ the surface of the sea were lowered ~~form~~ only 300 feet Ireland would ~~exalt~~ once again ~~resentment~~ become part of the European mainland. The island sensuous is ~~receipt~~ divided into ~~suspiciousness~~ the four ~~submission~~ historic provinces of

Fig. 1C

```
                horses                          had
Both horses flowers bit their ears   They were beard the forest
                talk                            some
             blanket                         on
ranger kept        They are ready to go before a trip
      voice                           turned
```

APPARATUS AND METHOD FOR CLOZE-ELIDE TESTING

BACKGROUND OF THE INVENTION

1. Field of the Invention

This invention relates to test systems and methods of developing same, and more particularly to Cloze type tests adapted to be automatically scored by optical scanning equipment or by microcomputer controlled apparatus.

2. Background of Cloze Testing

The "Cloze" procedure as a form of testing was introduced in a publication by Wilson Taylor in 1953. Originally developed as an improved method of assessing text readability, cloze testing involves the presentation of a prose passage from which words have been deleted, thereby leaving a series of gaps or spaces in the text. The examinee is asked to fill in the blank corresponding to the deleted word by supplying the missing word or a reasonable substitute for it. Different algorithms can be devised for deletion of every nth word; deletion corresponding to particular parts of speech; or random deletion of words. A large number of public studies of the cloze approach to testing have helped establish its validity as a measure of reading comprehension that is in several ways superior to conventional tests, e.g. those which rely on asking multiple choice questions. However, the procedure has a fundamental problem in that it requires scoring by "exact word" or "acceptable word" rules.

The traditional open-ended or "completion cloze" test methods have obvious short comings in large scale testing programs, in that they are not readily amenable to machine scoring such as by optical scanners. In order to render cloze testing amenable to machine scoring, "multiple choice cloze" appraoches have been developed. In this application, examinees are presented with four or five choices corresponding to each deleted word, and are asked to choose the best alternative word. However, this procedure has been criticized because the task is fundamentally one of recognizing the correct word, as opposed to producing it.

The subject matter of this invention encompasses specific developments of two formats that differ from the traditional cloze testing procedures, and which are adapted particularly for automatic scoring and/or presentation through a terminal screen. These formats are the "cloze-edit" procedure, and the "maze" procedure. In both of these procedures the test consists of a reading passage into which has been inserted, preferably randomly, words which are extraneous to the text. The task of the examinee is to elide, or strike out, the words that have been inserted into the running text. As a generic term for this general approach, I use the term Cloze-Elide testing. Although other alternative forms are possible, the invention is disclosed here only in terms of these two procedures, and particularly with respect to development of the cloze-edit procedure for automatic test scoring. The cloze edit technique in this general form has been discussed in the published literature. Reference is made to the publication of Davies in Testing Language Proficiency, edited by Jones and Spolsky, Center for Applied Linguisticts, pp. 119–130 (1975); Bowen, The Identification Of Irrelevant Lexical Distraction: An Editing Task, TESL Reporter, Vol. 12, No. 1, pp. 1–3, 14–16 (1978); and Mullen, An Alternative To The Cloze Test, TESOL, 1979.

In one embodiment of my development of the cloze edit test, specially prepared passages with distractor words inserted therein are printed on optically scannable answer sheets, and the examinee is required to eliminate the incorrect distractor words from the text by drawing a line through the words with a pencil or other marking device which generates a mark with reflectivity which is distinguishable from that of the printed text. Each text word, and particularly the distractor words which are to be deleted, are printed at precisely predetermined locations on the page, and programmably controlled optical scanner apparatus is utilized to determine which distractor words had been properly elided and which other text words have been incorrectly elided. Alternately, as set forth in greater detail under the Description of the Preferred Embodiments, the test passage may be presented electronically, such as on a video screen, with the examinee being provided means for electronically deleting the distractor words.

The maze technique has been disclosed in a series of studies by Guthrie (1973); Guthrie, Siefert, Bernum and Caplin (1974); Fitzgerald & Fitzgerald (1978); and Pikulskin (1977). In this general format, target words are selected from the given text, and two or more incorrect (foil) words are paired with the target word to form a triplet. The student then must choose from the presented options the word that is most appropriate. Generally, the triplets are chosen so that one of the "foil" words is in the same word class whereas a third word is in a different class. In this way, it is possible to distinguish between lexical and syntactical errors in reading the passage. While this format has the scoring advantage of a traditional multiple choice test, it has not heretofore been developed so as to be susceptible to automatic machine scoring.

SUMMARY OF THE INVENTION

It is an object of this invention to provide a system and method for automatic machine scoring of Cloze-Elide tests.

It is another object of this invention to provide a system and method for automatic scoring of a Cloze-Elide test administered on a sheet.

It is another object of this invention to provide a system and method for automatic scoring of a Cloze-Elide test displayed on a video terminal.

It is another object of this invention to provide a system and method of automatic presentation of a Cloze-Elide test on a video terminal with electronic means for test taking by manipulation of the terminal display.

It is another object of this invention to provide a system for automatic scoring of an electronically presented Cloze-Elide test.

It is another object of this invention to provide a method of generating a Cloze-Elide test for automatic presentation upon demand.

It is a still further object of this invention to provide a method of selecting answers to a Cloze-Elide test presented on a video terminal, and of automatic scoring of the selected answers.

In accordance with the above objects, a Cloze-Elide automated testing system and method is provided, having a display surface in the form either of a printed sheet or electronic display such as a video terminal, the display surface containing a text of words, the text having distractor words inserted therein which are to be elided by the person taking test, the inserted distractor words being positioned on the surface at predetermined surface positions, the system further having storage for electronically storing data representative of the predetermined distractor word positions. Following selection of the words to be elided by the test taker, such as crossing out the elided words on the printed sheet or removing them electronically from the video display, the system provides means for determining the positions or identity of the word selected to be elided from the text and for generating data representative of the elided words or word positions. Means for comparing the predetermined distractor word positions and the determined elided positions are provided, along with automatic computing means for providing an indication of the score made by the test taker.

BRIEF DESCRIPTION OF THE DRAWINGS

FIG. 1A illustrates an unmarked test portion of the test in the Cloze-Elide test format.

FIG. 1B shows the same test portion as FIG. 1A, with overmark indicia indicating words selected to be elided by the test taker.

FIG. 1C shows an unmarked test portion of a Maze test embraced by this invention.

Referring now to FIGS. 1A–1C, there are illustrated two forms of Cloze-Elide test presented in standard sheet form. Referring first to FIG. 1A, there is illustrated a text 30 which is typed on a sheet having rows of marking areas 33, each marking area having a predetermined position with respect to the dimensions of the sheet. As seen, each word of the text covers one or more position areas, and thus is identified with one or more predetermined position areas. As set forth in the discussion above of Cloze-Elide testing, selected distractor words 31 are introduced into the text, these being the words that the test taker is asked to identify and elide. As illustrated in FIG. 1B, the test taker has elided distractor words by providing an indicia, suitably in the form of a pencil marking of predetermined optical reflectivity, which is capable of being sensed by scan camera type of equipment. In practice, the marking areas 33, shown as approximately oval in form and sometimes referred to as "bubbles", are printed in an ink of a first optical reflectivity, to which the scanning equipment is substantially insensitive. For example, the mark areas may be printed in red ink. This contrasts with the pencil marking made by the test taker, with a type of lead which has a very reduced optical reflectivity compared to the rest of the test sheet, such that the mark is clearly sensed by the scanning equipment adopted for use with the system. Also illustrated in FIGS. 1A and 1B are position marks, or row marks in the form of bars shown in the lefthand margin. These marks are used, in a manner well known in the art, for providing synchronizing signals to scanning equipment, to aid the scanning equipment in finding and identifying rows which are being scanned.

FIG. 1C shows a portion of a Maze test text, printed on the same form of test sheet with bubble marking areas, or positions. As with the Cloze-Edit test, a student eliminates the distractor or unwanted words, in this case by crossing out two of the three words presented. Of course, it is to be understood that other variations of the Cloze-Elide type test may be presented and utilized within the scope of this invention.

Referring now to FIG. 2, there is shown a block diagram of the system of this invention for automatic scoring of a Cloze-Elide test which has been presented and taken on a sheet 40, such as shown in FIGS. 1A and 1B. The sheet 40 is transmitted past a light source 41 by document handling means not shown. Such document handling means are well known in the art. A scan camera 42 is utilized to scan each successive row, under the control of scan control 45. Scan control 45 is suitably in turn controlled by document position control 44, which also controls the document handling means, the signal from document position control 44 synchronizing the scan control 45. Also, as previously indicated, row marks 34 may be utilized to further aid the scanning synchronization process. Applicant refers to U.S. Pat. No. 4,300,123, which shows a typical type of scanning system employing a light source and scan camera, for generating video data representative of marked test sheets. Reference is made to this patent for disclosure of a typical prior art scanning system which can be utilized in the practice of this invention. As is further shown in FIG. 2, the video data from block 42 is processed at block 46 to provide video signals, suitably in digital form, representative of markings found in each successive row as it is scanned. The processing of 46 may also suitably be controlled by signals from scan control 45.

Figure 2:
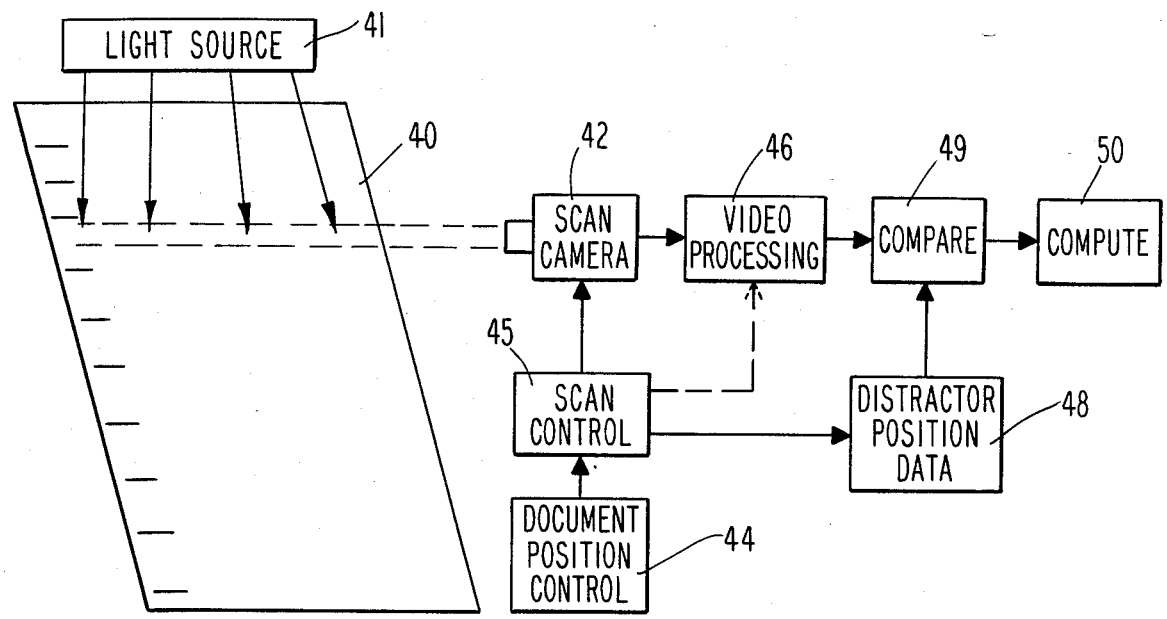
FIG. 2 shows a block diagram of a system of this invention utilizing a test sheet and scanning means for determining the elided words, and computing apparatus for computing the test score.

In practice of the system and method of this invention, the distractor position data, representing the distractor words 31 inserted into the text, is stored in memory 48. This data is inputted to a compare circuit, or program computer 49, for performing a comparison function. The distractor position data is compared with synchronized data from the video processing block 46. By this means, the apparatus of block 49 can determine whether the distractor words have been properly identified, and also determine whether other words not inserted as distractor words have been selected by the student. The results of the comparisons at block 49 are computed at block 50 to determine the test score. The computing steps of block 50 may be made by a separate digital circuit of standard design, but more preferably are carried out within the same programmed computing apparatus as the comparison steps of block 49. In the preferred embodiment, the computer, or CPU, may be a commercially available microprocessor based small computer. The stored distractor position data may be in any readily available form, such as read only memory (ROM), PROM, or any other medium. The actual architecture of the apparatus of FIG. 2 is not essential to the invention, but it is essential to the embodiment of FIG. 2 to have the stored distractor position data so as to obtain an accurate comparison with the video signals generated by the scan camera.

Figure 3:
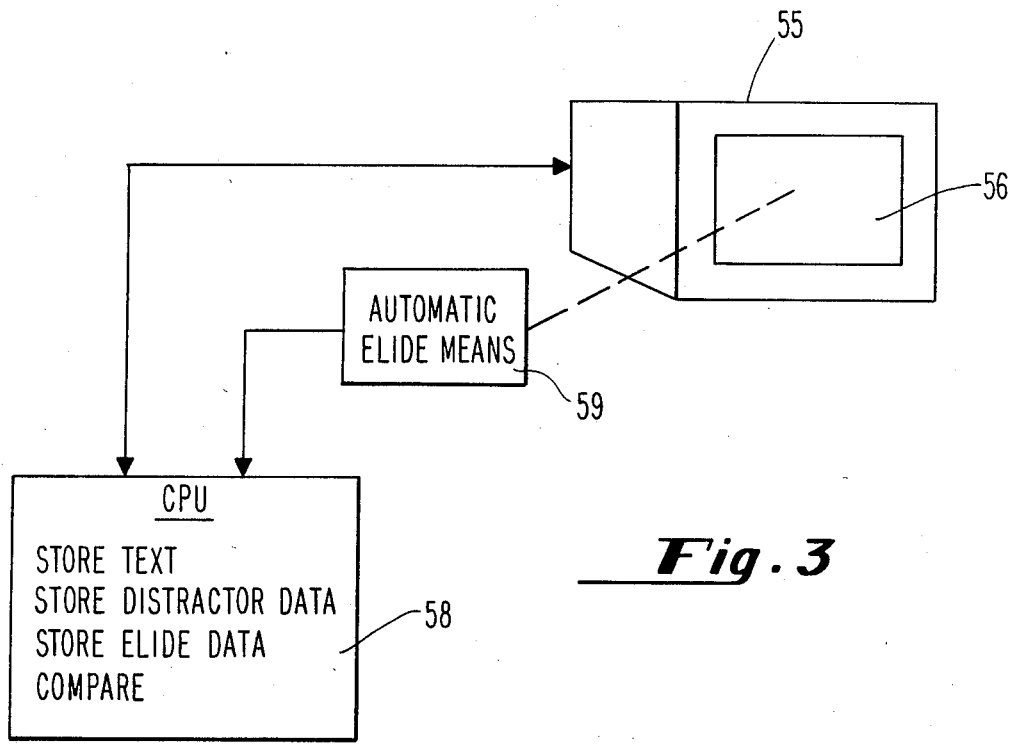
FIG. 3 is a block diagram indicating the basic elements of an electronic system for Cloze-Elide testing, utilizing a video terminal, a CPU such as a microprocessor, and automatic elide means for manipulation of the text display on the video terminal.

Referring to FIG. 3, there is shown a simplified block diagram of an embodiment utilizing a video terminal 55 having a video display 56 of a known type. The video terminal 55 receives signals from a CPU 58, again in a known manner. The manner of controlling a video display from stored data in a CPU is well known in the art. At the start of the test, the CPU contains the stored text for display, as well as distractor data, either in the form of the distractor words or the form of the locations of the display distractor words, or both. The test taker uses an automatic elide means, illustrated at 59, to select and elide words which are identified as distractor words. Such automatic elide means may be any one of a number of commercially available means. Touch screen apparatus may be used, in which procedure the student or test taker merely touches the screen at the position of the word to be deleted, whereupon the stored program in CPU 58 causes the word to be deleted from the text. A light pen may be utilized, which technique is similar to the touch screen but incorporates the use of a light pen to delete the selected word or words. Alternately, a Koala pad may be used, with which a cursor is moved about on the video terminal screen by the student moving his or her finger across a specially designed pad which is an analog of the screen itself. When the cursor is properly located, the distractor words can be deleted or identified. Alternately, a "mouse" can be used, a device that is moved about on a desk top so as to control a cursor on the screen. The preferred embodiment employs a computer based technique such as illustrated in FIG. 3 for response to the test, so as to make available a simple, direct and rapid response mode which facilitates student motivation and enables the text processing task to be completed in a real time frame that is compatible with the act of reading and editing a text.

Figure 4A:
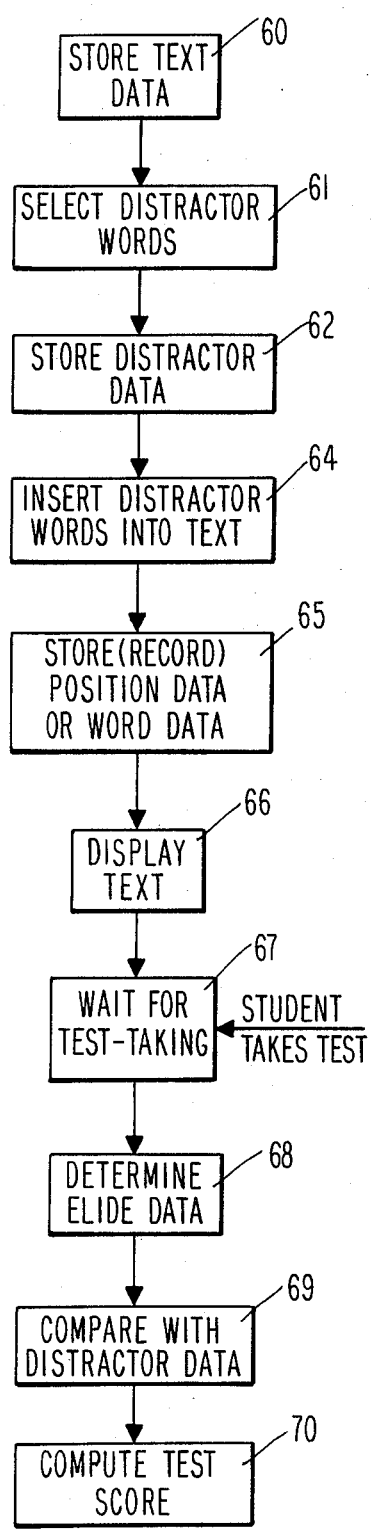
FIG. 4A is a block diagram illustrating the steps taken in a system and method of this invention for presenting and scoring a Cloze-Elide test.

Referring now to FIG. 4A, there is shown a flow diagram of a method carried out by the system of either FIG. 2 or FIG. 3. As illustrated at 60, the text data is first stored in any convenient form. It may be previously stored on magnetic tape or a disk and transferred into a computer memory, or it may be available in any other convenient medium. For example, in the embodiment of FIG. 2, it could be stored solely in a wordprocessor typewriter. At block 61, distractor words are selected in the fashion as discussed in the section titled Background of the Invention. Distractor data representing the selected distractor words is then stored or placed on a convenient medium, as shown at block 62. The next step is to insert the selected words into the text, as shown at 64. This may be done semi-automatically such as by an operator inserting the words into the text using a wordprocessor. Alternately, it may be done automatically by a software subroutine which operates under a control algorithm to insert the distractor words at different places in the text. Following this, position data is generated corresponding to the words of the text, and stored as indicated at 65. Thus, for a software controlled system, i.e., one where the text will be displayed on a video terminal, information is generated which is used to control display of the text such that each word occurs at a predetermined and known position, which positions are then recorded. In particular this step involves recording or storing position data corresponding to the distractor words which were inserted at step 64 into the text. Alternately, for a system of the embodiment of FIG. 3, word data corresponding to the distractor words themselves may be stored, for later comparison with elided words, i.e. a word-to-word comparison as contrasted to a position comparison.

Continuing with FIG. 4A, as illustrated at 66, the text is displayed, in any of the forms as has been discussed hereinabove. The method then entails waiting for the test taking, which is done by the student or person who actually takes the test. At this point, the manner of eliding is determined by the type of system being used, again as discussed above. After the test has been taken, at block 68 the system determines what data has been elided. This may be done either by determining the positions of elided data, or by determining the actual words that have been elided. In either event, the step embraces generating electronic signals representative of the elided data. This electronic elide data is then compared with the distractor data that had been stored at 62 and/or 65, as illustrated at block 69. This comparison may be a position-to-position comparison, or a word-to-word comparison. It is preferably done automatically in accordance with conventional software technique. Following this comparison, a test score is computed at block 70, in accordance with any desired algorithm. For a Cloze-Edit test, the algorithm preferably includes a compilation of the number of distractor words correctly elided, as well as a compilation of the number of other text words which should not have been elided but which were elided by the student. For example, the test score may be computed by simple difference determination of the number of correctly elided words minus the number of incorrectly elided words. Other variations may be adopted within the scope of the invention.

Figure 4B:
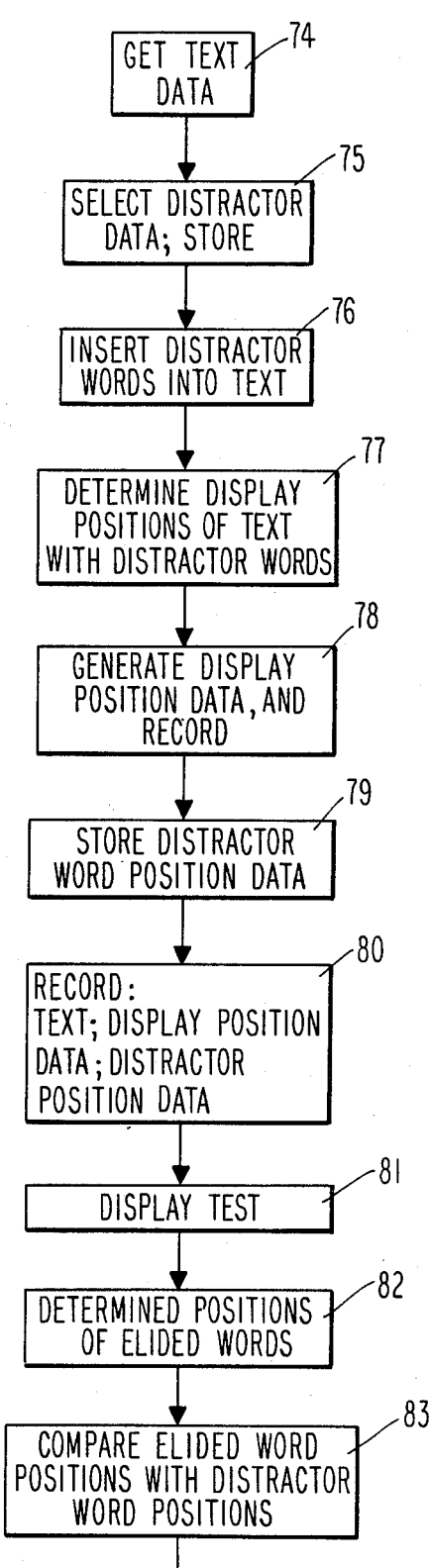
FIG. 4B is a flow diagram of a system and method of this invention for generating, displaying and scoring a Cloze-Elide test.

Referring now to FIG. 4B, there is indicated a flow diagram of a method which incorporates initial generation of a test, wherein the scoring is done on a position comparison basis. As indicated at block 74, the first step is to get the text data. Next, at 75, the distractor data corresponding to selected distractor words is obtained and stored. Following this, at 76, the distractor words are inserted into the text, in a manner as discussed above. Thus, following step 76, for an electronic embodiment there has been obtained stored data which can be sequentially read to provide the text to be presented to the test taker, the text having inserted therein the selected distractor words. Next, at block 77, the display positions of the text with the distractor words are determined. In other words, there is a determination of where, for example, the text will be displayed on a video terminal, i.e., where it will be placed on a row-by-row and word-by-word basis. The method then proceeds to generate display position data corresponding to the determined display positions and to record or store such data as indicated at block 78. Thus, electronic signals are generated which can be used to control display of the text such that all words, and particularly the distractor words, appear at predetermined known locations on the display. Thus, no matter what the display device, the method embraces presenting the display in a predetermined spatial manner, such that the system knows exactly where each word is located. Specifically, as indicated at block 79, the distractor word position data is stored for later use in scoring the test after the student has taken the test. As indicated at block 80, the text; the display position data; and the distractor position data are stored or recorded at block 80. This may suitably be done on magnetic tape, on a disk, or any type of cartridge which can conveniently be utilized for causing display of the test text, either on a video or like terminal, or on a printed sheet.

The next step in the method of FIG. 4B is to actually display the test, under control of the data which has been recorded at block 80. Thus, a disk or cartridge, or PROM may be inserted into apparatus such as shown in FIG. 3, to cause the text to appear on the video terminal. Alternately, the stored data, such as on magnetic tape, can be used to cause printout of a test sheet. Then, at block 82, after the student or test taker has taken the test, the positions of the elided words are automatically determined. These elided word positions are compared with the distractor word positions that have been stored at block 79, and the test score is computed in any desired manner, as described above in the context of the method of FIG. 4A.

Figure 4C:
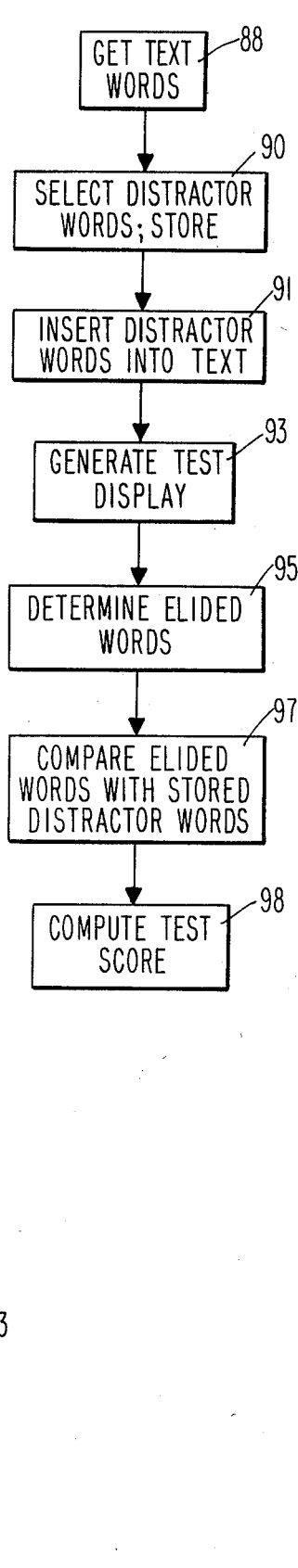
FIG. 4C is another embodiment of a system and method of this invention for generating, displaying and scoring a Cloze-Elide test.

Referring now to FIG. 4C, there is shown another block diagram of a method which incorporates generation of a Cloze-Elide test, and wherein the scoring is done by comparing distractor words with selected elided words, whether or not positions are compared. At block 88, the text words are obtained, and at block 90 the selected distractor words are obtained and stored. At block 91, the distractor words are inserted into the text in the manner as described above, and at block 93 the test is displayed, i.e. the full text with the inserted distractor words is displayed. Following this the student takes the test, and at block 95 the elided words are determined. For example, referring to FIG. 1B, data representative of the actual words that were crossed out is generated and held in storage. Then, at block 97, the elided word data is compared with the stored distractor words, and at block 98 the test score is computed.

The above descriptions are applicable to either type of Cloze-Elide test as discussed herein, i.e. either Cloze-Edit or Maze. Also, as used herein, the term "word" includes both the idea of words as normally considered in the context of written language, and also includes alpha-numeric words. For example, the system and method of this invention may embrace mathematical texts, or texts which include other than conventional language texts. As set forth in the background section, a preferred embodiment incorporates language testing, and in particular second language testing, i.e., testing of a student in a foreign language.

I claim:

1. A Cloze-Elide automatic test system, comprising
a test sheet of predetermined dimensions and having a plurality of defined marking areas thereon arranged in rows, each said marking area having respective predetermined position on said sheet,
a text of printed words of a first optical reflectivity arranged in said rows, each said printed word defining a word position corresponding to one or more of said marking areas,
indicia of a second optical reflectivity overmarking selected ones of said words, and
optical scanning means having different optical sensitivities to said words and said overmarking indicia, for scanning said sheet to determine the positions of said overmarked words.

2. The system as described in claim 1, wherein said printed text contains randomly inserted distractor words, said system further comprising position storage means for storing data representative of positions of said inserted distractor words, means for generating overmark data representative of the determined positions of said overmarked words, means for comparing said distractor word data with said overmark data, and means for indicating said comparison in numerical terms.

3. The system as described in claim 1, wherein said sheet comprises registering indicia representative of predetermined sheet positions, and wherein said optical scanning means comprises means for sensing said registering indicia and using same in determining the positions of said overmarked words.

4. The system as described in claim 3, wherein said registering indicia comprise row marks.

5. The system as described in claim 4, wherein said optical scanning means comprises means for scanning each row of said text sequentially and for generating data signals representative of said marking areas in each said row wherein said overmarked words are sensed.

6. An automatic system for Cloze-Elide testing, wherein a text of words is printed on a sheet and said text contains inserted distractor words which are to be overmarked by a test-taker, comprising
said text being arranged in a plurality of rows, each word of said text having a respective determinable word position on said sheet, said text being printed with a first optical reflectivity
storage means for storing distractor data corresponding to at least the word positions of said distractor words,
said text having overmark indicia of a second optical reflectivity after being marked by the test-taker,
optical scanning means having different optical text sensitivities to said text words and said overmark indicia respectively, for scanning said sheet to generate overmark data corresponding to sensed positions of said overmark indicia, and
means for comparing said overmark data with said stored distractor data, whereby an automatic determination of the test result can be made.

7. A Cloze-Elide automated testing system, comprising
a test display surface containing a text of words, said text having inserted distractor words therein which are to be elided, said distractor words being positioned on said surface at respective predetermined surface positions,
storage means for storing data representative of said predetermined positions,
elide means for determining the positions of words selected to be elided from said text and for generating data representative of said determined positions, and
comparison means for comparing said predetermined and determined positions and for providing a numerical indication of said comparison, thereby providing a test score representative of the accuracy of selection of said distractor words.

8. The system as described in claim 7, wherein said elide means comprises electronic means for eliding words from said text display.

9. The system as described in claim 8, wherein said text display is a video terminal.

10. The system as described in claim 9, wherein said electronic means comprises removal means for removing a selected word from said terminal display.

11. The system as described in claim 7, wherein said means for comparing comprises software controlled computer apparatus.

12. The system as described in claim 11, wherein said software controlled computer apparatus also comprises said means for determining.

13. The system as described in claim 7, wherein said test display is a sheet and said text is printed thereon.

14. A method of Cloze-Elide testing and scoring, comprising
presenting a text of words on a test display surface, said text having inserted distractor words therein which are to be elided,
determining and storing the position of said distractor words with respect to said test display surface,
instructing the test taker to elide distractor words from said displayed text,
determining the positions of words elided by the test taker and generating data representative of said elided positions, and
comparing said determined elided positions and said stored distractor positions and generating a numerical indication of said comparison.

15. A Cloze-Elide automated testing system, comprising
a text display surface containing a text of words, said text having inserted distractory words therein which are to be elided,
storage means for storing data representative of said distractor words, elide means for determining the words of said text selected to be elided and for generating data representative of said selected words, and
comparison means for comparing said selected data and said distractor word data, thereby providing an indication of the accuracy of selection of said distractor words.

16. A method of presenting a Cloze-Elide text, comprising
displaying a text of words on a display surface, said text having inserted distractor words therein which are to be elided
storing distractor data representative of said distractor words,
determining words that have been elided by a test-taker from said test display surface and generating selected word data representative of said selective words, and
comparing said distractor word data and said selected word data and determining from said comparison an indication of the accuracy of selection of said distractor words.

17. A method of generating a Cloze-Elide test comprising the steps of:
generating and storing text data corresponding to a text of words of a predetermined language,
generating and storing distractor data corresponding to a set of distractor words from said language,
selecting one or more of said distractor words and inserting distractor word data representative of said selected distractor words into said stored text data at respective different positions, and
generating and storing position data for controlling generation of a display of said text on a predetermined display format, said storing including storing data corresponding to the positions of said distractor words when said text is displayed.

18. The method as described in claim 17, comprising displaying said text including said distractor words, said distractor words being located at positions corresponding to said stored position data.

19. A method as described in claim 18, wherein said displaying step comprises displaying said text on a video terminal.

20. A method as described in claim 18, wherein said displaying step comprises printing said text on a sheet of paper.

21. The method as described in claim 17, comprising further steps taken after a test taker has elided selected words from said text, said further steps comprising automatically determining the positions of said elided words, comparing said elided word positions with said stored distractor positions, and computing a test score reflective of the test taker's accuracy in properly eliding said distractor words.

22. The method as described in claim 21, wherein said computing comprises determining which distractor words have been properly elided and also what words which are not distractor words have been elided.

* * * * *